(12) United States Patent
Sun et al.

(10) Patent No.: US 10,709,418 B2
(45) Date of Patent: Jul. 14, 2020

(54) ULTRASOUND DIAGNOSTIC APPARATUS WITH EASY ASSEMBLY AND DISASSEMBLY

(71) Applicant: CHISON MEDICAL IMAGING CO., LTD., Wuxi, Jiangsu (CN)

(72) Inventors: Dongdong Sun, Wuxi (CN); Chunlin Peng, Wuxi (CN); Jian Lu, Wuxi (CN)

(73) Assignee: CHISON MEDICAL TECHNOLOGIES CO., LTD., Wuxi (CN)

( * ) Notice: Subject to any disclaimer, the term of this patent is extended or adjusted under 35 U.S.C. 154(b) by 913 days.

(21) Appl. No.: 15/311,115

(22) PCT Filed: Mar. 9, 2016

(86) PCT No.: PCT/CN2016/075919
§ 371 (c)(1),
(2) Date: Nov. 14, 2016

(87) PCT Pub. No.: WO2016/141874
PCT Pub. Date: Sep. 15, 2016

(65) Prior Publication Data
US 2017/0086787 A1    Mar. 30, 2017

(30) Foreign Application Priority Data

Mar. 10, 2015 (CN) .......................... 2015 1 0105029
Sep. 30, 2015 (CN) .......................... 2015 1 0640528

(51) Int. Cl.
*A61B 8/00* (2006.01)
*A61B 8/14* (2006.01)
*A61B 8/08* (2006.01)

(52) U.S. Cl.
CPC .............. *A61B 8/4411* (2013.01); *A61B 8/00* (2013.01); *A61B 8/14* (2013.01); *A61B 8/4405* (2013.01);
(Continued)

(58) Field of Classification Search
None
See application file for complete search history.

(56) References Cited

U.S. PATENT DOCUMENTS 4,483,178 A * 11/1984 Miille .................. G01D 5/42
                                                361/679.31
5,515,853 A *  5/1996 Smith .................. A61B 5/0422
                                                600/437
(Continued)

FOREIGN PATENT DOCUMENTS

CN      201119884 Y      9/2008
CN      101438965 A      5/2009
(Continued)

OTHER PUBLICATIONS

PCT International Search Report and Written Opinion dated May 18, 2016, issued in corresponding International Application No. PCT/CN2016/075919 (12 pages).

*Primary Examiner* — Katherine L Fernandez
(74) *Attorney, Agent, or Firm* — Finnegan, Henderson, Farabow, Garrett & Dunner LLP (57) ABSTRACT

The present disclosure includes an ultrasound diagnostic apparatus with easy assembly and disassembly. The apparatus comprises an outer casing including a motherboard module having motherboard guiding plugs and motherboard ports installed thereon and a first outer-casing sliding device; and a main case structure being housed by the outer casing, including a transducer panel module coupled to an I/O module, a carrier board module coupled to the transducer panel module via the I/O module and having a PC module installed thereon process ultrasound data, carrier-board guiding holes to receive the motherboard guiding plugs, carrier-board ports to inter-plug in the motherboard ports, and a first main-case sliding device to slide in the first outer-casing sliding device and facilitate the main case (Continued)

structure to move relative to the outer casing; wherein the motherboard module and the I/O module are perpendicular to the transducer panel module and the carrier board module.

20 Claims, 10 Drawing Sheets

(52) U.S. Cl.
CPC ............ *A61B 8/4483* (2013.01); *A61B 8/467* (2013.01); *A61B 8/5207* (2013.01); *A61B 8/54* (2013.01); *A61B 8/56* (2013.01)

(56) References Cited

U.S. PATENT DOCUMENTS

| | | | |
|---|---|---|---|
| 2007/0061435 A1* | 3/2007 | Di Cristofano | G06F 1/18 709/223 |
| 2008/0194960 A1 | 8/2008 | Randall | |
| 2010/0177080 A1* | 7/2010 | Essinger | G06F 3/147 345/211 |

FOREIGN PATENT DOCUMENTS

| | | |
|---|---|---|
| CN | 202283259 U | 6/2012 |
| CN | 203341753 U | 12/2013 |
| CN | 104203138 A | 12/2014 |
| JP | 2012-197074 A | 10/2012 |

\* cited by examiner

ULTRASOUND DIAGNOSTIC APPARATUS WITH EASY ASSEMBLY AND DISASSEMBLY

CROSS REFERENCE TO RELATED PATENT APPLICATIONS

This international application claims the priority and benefit of Chinese Application No. 201510105029.0 filed on Mar. 10, 2015 and titled "Ultrasound Diagnostic Device with Easy Assembly and Disassembly," and Chinese Application No. 201510640258.X, filed Sep. 30, 2015 and titled "Ultrasound Diagnostic Device with Easy Assembly and Disassembly," both of which are incorporated in their entirety by reference herein.

TECHNICAL FIELD

The present disclosure relates to ultrasound diagnostic devices in general and, more particularly, to ultrasound diagnostic apparatus with easy disassembly and assembly, which improve performance and allow easy disassembly and assembly.

BACKGROUND

Ultrasounds refer to sound waves with frequencies higher than the upper limit of human adult hearing, an average of which is approximately 20,000 hertz. Ultrasounds have been used in various fields, including therapeutic and diagnostic fields. One popular diagnostic application is ultrasound imaging, which creates images of internal body structures, such as internal organs, vessels, bones and muscles, etc. When ultrasounds pulses are sent into tissues inside the body, due to the different acoustic impedances of the tissues, the ultrasounds will be reflected anywhere there are changes in the acoustic impedance. The return sound waves will be converted into electrical pulses and processed into a digital image for display. For example, obstetric/prenatal ultrasound is a widely used technique in pregnancy examination, which uses ultrasound waves to create visual images of the developing embryo or fetus in the mother's womb.

Conventional ultrasound diagnostic devices usually have a computer with a large sized case having different components installed therein. Those components are scattered inside the case and are connected by various cables. In the conventional ultrasound diagnostic devices, however, the scattered distribution and assembly of various components and connecting cables may interfere transmission of ultrasound and electrical pulses. In addition, the structural layout in the conventional ultrasound diagnostic devices may negatively affect heat dissipation, compromising overall device performance and imaging quality. Moreover, the above scattered layout makes it difficult and inconvenient for a technician to maintain, inspect, and repair components inside the computer case. For example, inspection and repair of certain components often requires disassembly of neighboring components, sometimes even the whole device. Furthermore, as some components are permanently secured onto an interior surface of the casing or manufactured as part of the casing, repair personnel often have to squat down to reach the components inside the casing.

Thus, there is a need to develop ultrasonic diagnostic systems and apparatus that reduce interferences in ultrasonic and electrical pulses, provide efficient heat dissipation, allow easy disassembly, assembly, and maintenance, and overcome the limitations of conventional ultrasound diagnostic devices.

SUMMARY

The present disclosure includes an exemplary ultrasound diagnostic apparatus with easy assembly and disassembly. Embodiments of the apparatus comprise an outer casing, which includes a motherboard module having one or more motherboard guiding plugs and one or more motherboard ports installed thereon to facilitate the assembly, and a first outer-casing sliding device. Embodiments of the apparatus also comprise a main case structure being housed by the outer casing. The main case structure includes an I/O module, a power-supply module to receive a power supply and provide the power supply to the ultrasound diagnostic apparatus, a transducer panel module coupled to the I/O module and having a transceiver and a transducer information-processing module installed thereon, the transceiver being coupled to a transducer to emit and receive ultrasound electrical signals and the transducer information-processing module converting the received ultrasound electrical signals into digital information. The main case structure also includes a carrier board module coupled to the I/O module and to the transducer information-processing module via the I/O module and having a PC module installed thereon to process the converted digital information and transmit the processed digital information to an output device coupled to the one or more motherboard ports, the PC module being coupled to the motherboard module. It further includes one or more carrier-board guiding holes to receive the one or more motherboard guiding plugs and guide the assembly, one or more carrier-board ports to inter-plug in the one or more motherboard ports and facilitate data communications between the motherboard module and the carrier board module, and a first main-case sliding device to slide in the first outer-casing sliding device and facilitate the main case structure to move relative to the outer casing along the first outer-casing sliding device during the assembly and disassembly. In the embodiments of the apparatus, the motherboard module and the I/O module are installed on the main case structure's two opposite sides perpendicular to the transducer panel module and the carrier board module to allow the easy assembly and disassembly.

It is to be understood that both the foregoing general description and the following detailed description are exemplary and explanatory only and are not restrictive of the invention, as claimed.

DETAILED DESCRIPTION

Reference will now be made in detail to the exemplary embodiments illustrated in the accompanying drawings. Wherever possible, the same reference numbers will be used throughout the drawings to refer to the same or like parts.

Apparatus disclosed herein address the above described needs. For example, exemplary embodiments include a main case structure and an outer casing housing the main case, wherein through one or more mechanisms, such as sliding wheels, ball rollers, sliding bars, sliding slots, etc. the main case structure may move relative to the outer casing, and may further be detached from the outer casing when needed. For an accurate and secure connection during normal operation, the outer casing may include one or more positioning pins to be fitted into corresponding positioning holes on the main case structure. Alternatively, the main case structure may include one or more positioning pins to be fitted into corresponding positioning holes on the outer casing. As a result, the main case structure, along with the structural components installed inside, may be easily displaced and exposed for repair or maintenance. The outer casing may include a mother board containing a plurality of ports for connecting with a user display, an input device, a printer, and other devices. Some embodiments may include one or more insulation walls, one end of which may be secured onto an interior surface of the main case structure, to separate a transducer module and a processing module from each other. The insulation walls may be made of materials or coated with materials capable of reducing or substantially eliminating signal interference, such as zinc-coated metal sheets. As a result of signal interference prevention, the diagnosis accuracy and overall device performance may be improved. Still other embodiments may include a battery insulation wall, to further prevent signal interference from the batteries. A battery installing panel on which the battery is installed may be connected to the main case structure, facilitating easy removal and inspection.

Figure 1:
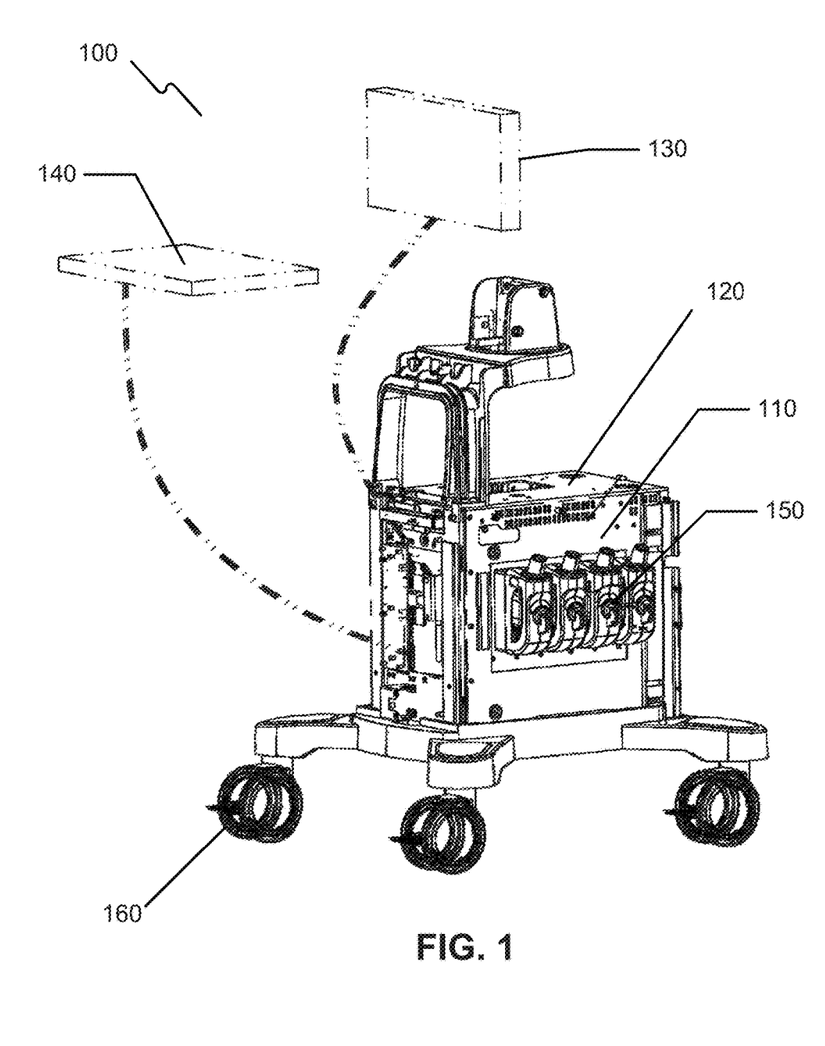
FIG. 1 illustrates an exemplary ultrasound diagnostic apparatus consistent with the present disclosure.

FIG. 1 illustrates an exemplary ultrasound diagnostic apparatus consistent with the present disclosure. The exemplary ultrasound diagnostic apparatus 100, as shown in FIG. 1, includes a main case structure 110, an outer casing 120, an output device 130, an input device 140, a transducer array 150, and apparatus wheels 160. Main case structure 110 is housed inside outer casing 120. Output device 130 and input device 140 are connected to some ports on outer casing 120. In some embodiments, output device 130 and input device 140 may be housed in one device. In some embodiments, apparatus 100 may include more than one output device 130 and input device 140.

In some embodiments, output device 130 is a display device, such as a computer monitor, a laptop, a desktop, a touch screen, a smart phone, a TV set, a projector, or any of other display devices. In some embodiments, output device 130 may be a printer, a fax machine, image processing equipment, an email device, or any of other output devices to output ultrasound analytical data. In some embodiments, apparatus 100 may include more than one output device 130. Output device 130 may present to the user various data relating to the performance and operation of the apparatus, such as record of the patient, information about the patient's organs undergoing ultrasonic diagnosis, information about operation modes, videos or pictures obtained from the ultrasonic diagnosis, and environment condition information such as temperature and humidity.

Input device 140 could be a keyboard, a touch panel, a tablet, a laptop, a desktop, or other input devices. Through input device 140, a user may input apparatus control parameters and operation instructions, such as parameters relating to transmission of ultrasound pulses (frequency, timing, angle, etc.), and parameters controlling operation conditions of the apparatus or output display.

Transducer array 150 may include one or more transducers. Transducers may convert electrical signals to ultrasound pulses, and vice versa. Transducer array 150 may include transducers of different shapes, sizes, or models. The transducers may use different frequencies, and contain various numbers of elements.

Apparatus wheels 160 support apparatus 100 on a movable horizontal platform. Embodiments of the present disclosure may also be used in other types of ultrasound diagnostic apparatus such as those placed on a fixed platform, or affiliated to a larger piece of medical equipment.

Figure 2:
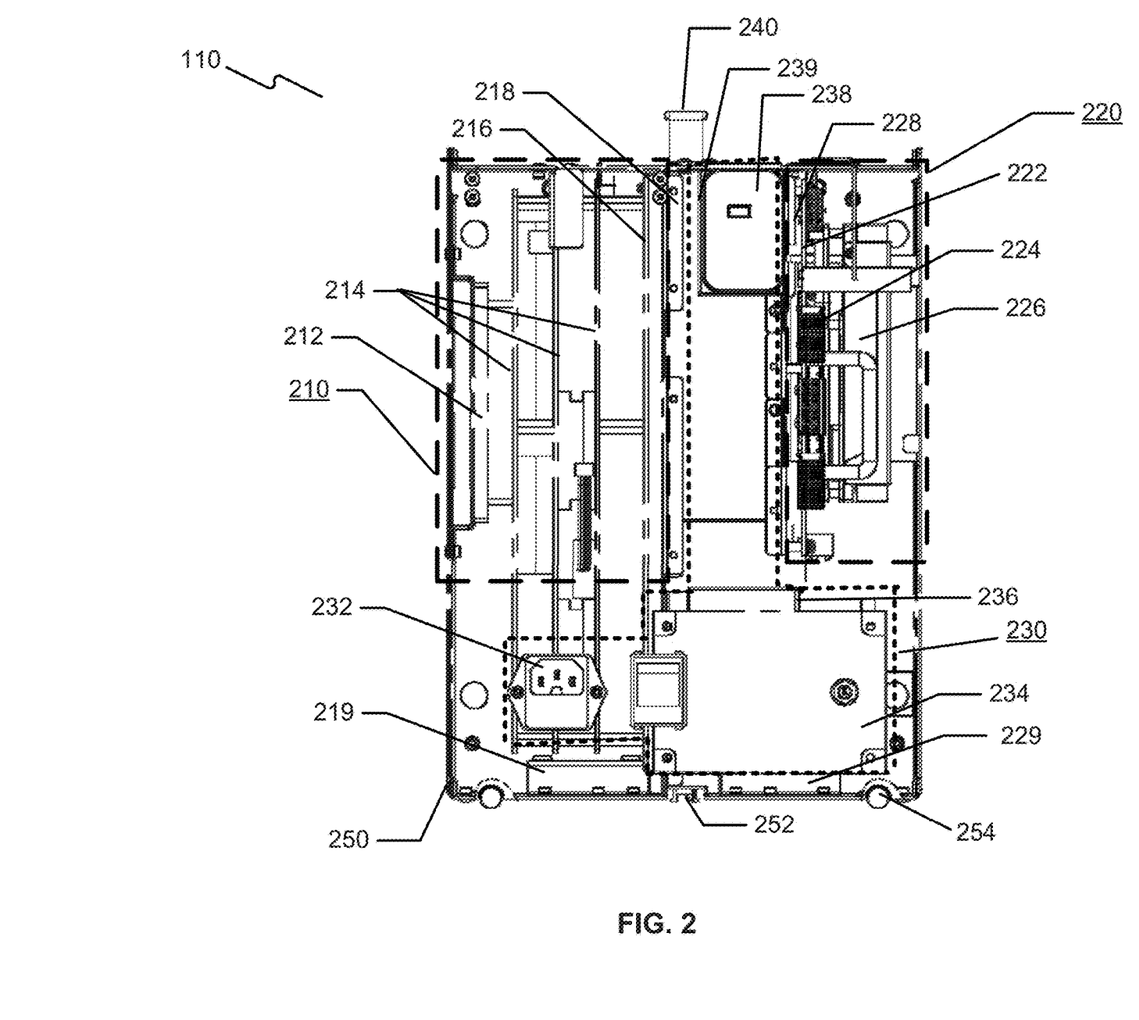
FIG. 2 illustrates a side view of an exemplary main case structure of the exemplary ultrasound diagnostic apparatus of FIG. 1.

FIG. 2 illustrates an exemplary side view of main case structure 110 of the exemplary ultrasound diagnostic apparatus of FIG. 1. As shown in FIG. 2, main case structure 110 includes a transducer module 210, a processor module 220, and a power module 230, each illustrated in a dashed box, respectively. In some embodiments, main case structure 110 may also include a transducer insulation wall 218.

In some embodiments, transducer module 210 may include one or more transducer ports 212, one or more transducer panels 214 having transducer ports 212 and one or more transceivers (not shown in FIG. 2) install thereon, and a transducer-panel baseboard 216 for installing the transducer panels 214. Transducer ports 212 may be coupled to transducers in array 150 of FIG. 1. Corresponding to the number and sizes of transducer ports 212 and transducers in array 150, main case structure 110 may further include one or more transducer windows (now shown in FIG. 2) through which the transducers in array 150 are connected to the transducer ports. Transducer panels 214 have one or more transducer ports 212, transceivers, and an information-processing module installed thereon. The transceivers can transmit or receive ultrasound electrical signals to or from an object under diagnosis. The information-processing module can convert the ultrasound electrical signals into digital information. Transducer-panel baseboard 216 is used to install transducer panels 214. Transducer-panel baseboard 216 may be permanently secured to or detachable from an interior surface of main case structure 110. Transducer-panel baseboard 216 may contain one or more materials capable of reducing or eliminating signal interference, such as zinc-coated metal sheets.

Transducer-panel baseboard 216 is installed on transducer insulation wall 218. Transducer insulation wall 214 is mounted onto an interior surface of main case structure 110 at one end portion or at both ends of structure 110, separating transducer module 210 and processor module 220 from each other and creating two relatively closed spaces. Transducer insulation wall 218 may contain one or more materials capable of eliminating or reducing signal interference between transducer module 210 and processor module 220, and interference from other components as well. For example, transducer insulation wall 218 may be made of zinc-coated metal sheets. Transducer insulation wall 218 may substantially surround transducer module 210, or alternatively substantially surround processor module 220, to improve signal interference prevention. In some embodiments, transducer insulation wall 218 divides an internal space of main case structure 110 into two relatively closed spaces vertically or horizontally, one closed space with transducer module 210 installed therein, and the other closed space with processor module 220 and power module 230 installed therein. In some embodiments, transducer insulation wall 218 may be of different designs and shapes, and may divide the internal space of main case structure 110 into spaces with different shapes and orientations.

In some embodiments, transducer module 210 may include one or more transducer fans 219, for heat dissipation purpose. In some embodiment, as shown in FIG. 2, transducer fans 219 are installed in a bottom section of main case structure 110. Corresponding to a position of transducers fans 219, one or more ventilation openings may be configured on the casing of main case structure 110. The size and design of the ventilation openings may vary, depending on the working environment conditions, and an overall design of the apparatus.

With reference to FIG. 2, in some embodiments, processor module 220 may include a carrier board module 222, a PC module 224 installed on module 222, a PC fan 226 installed on module 224, and a carrier-board baseboard 228 for installing module 222. In some embodiments, processor module 220 may include one or more carrier-board fans 229. In some embodiments, carrier-board fans 229 are located near a bottom of main case structure 110.

Processor module 220 is configured to process and store data and information including ultrasound signals, parameter information, and patient information. Module 220 may also generate ultrasonic image and video/audio signals for display to the user, and store and perform user instructions such as apparatus control parameters. Processor module 220 may include any elements that control and coordinate the operation of other parts of the ultrasound diagnostic apparatus 100, for example, a central processing unit (CPU), a microprocessor, a graphics processing unit (GPU), an application specific integrated circuit (ASIC), a field-programmable gate array (FPGA), a complex programmable logic device (CPLD), a printed circuit board (PCB), a digital signal processor (DSP), a memory, etc.

In processor module 220 as shown in FIG. 2, PC module 224 may have a PC fan 226 installed thereon for dissipating heat generated by components of PC module 224. In some embodiments, PC module 224 may include a memory or a hard drive for data storage, and a CPU or GPU for data processing and digital image generation. Carrier-board baseboard 228 is used to install carrier board module 222, which has PC module 224 and other components installed thereon. Baseboard 228 may include one or more materials capable of reducing or eliminating signal interference, such as zinc-coated metal sheets.

In some embodiments, processor module 220 may include one or more carrier-board fans 229 for dissipating heat generated from components installed on carrier board module 222. In some embodiments, as shown in FIG. 2, carrier-board fans 229 are located near a bottom of main case structure 110. Corresponding to the position of carrier-board fans 229, one or more ventilation openings may be configured on the casing of main structure 110. The size and design of the ventilation openings may vary, depending on working environment conditions and an overall design of the apparatus.

Figure 9A:
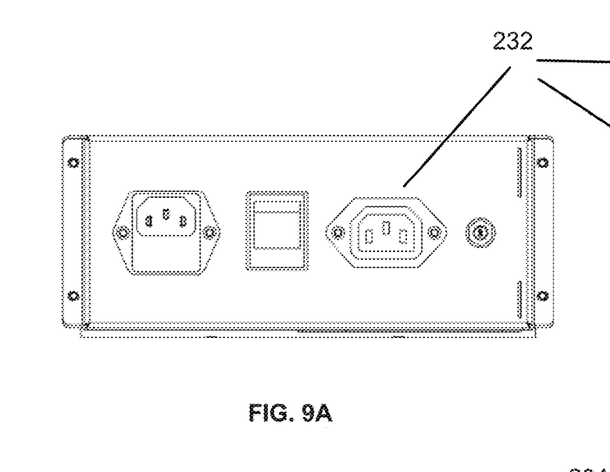
FIGS. 9A, 9B, and 9C illustrate part of an exemplary power module of an exemplary main case structure of FIG. 2.
Figure 9B:
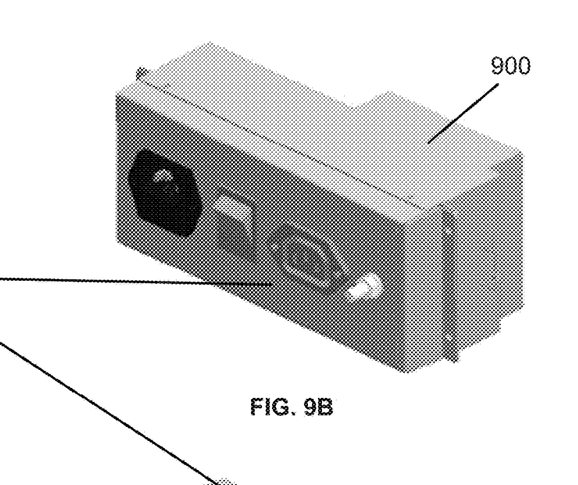
Figure 9C:
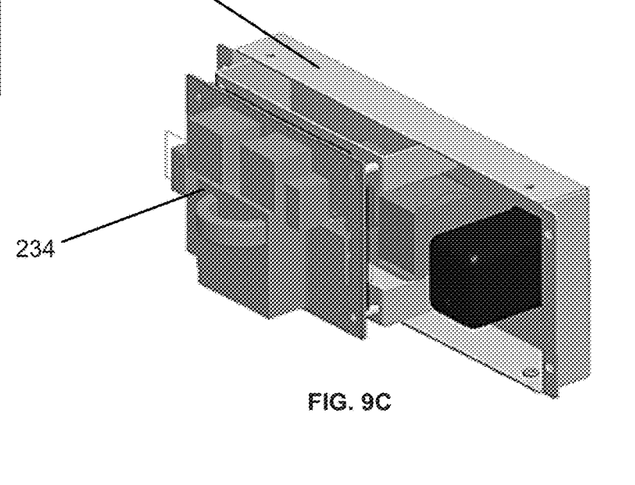

Still referring to FIG. 2, in some embodiments, power module 230 may include an AC-DC (alternating current to direct current) converter 232, a power-supply filter panel 234, and a power-supply adapter 236. AC-DC converter 232 includes an input power socket to receive a power supply in a form of an alternating current, and converts it to a direct current power supply. The converted direct current power supply is provided to power-supply adapter 236 for adapting to a voltage required by components installed in main case structure 110 and outer casing structure 120. In some embodiments, AC-DC converter 232 may also include an output power socket to provide a power supply in a form of an alternating current. FIGS. 9A-9C illustrate part of an exemplary power module 230 of an exemplary main case structure of FIG. 2. As illustrated in FIGS. 9A-9C, power-supply filter panel 234 may be installed on AC-DC converter 232 to insulate signal interference caused by converter 232. In some embodiments, Panel 234 and converter 232 may form a functioning module, which is placed in a relatively closed insulation box 900, as shown in FIG. 9B. The insulation box can further eliminate or minimize signal interference on other components installed in main case structure 110. In some embodiments, the insulation box is not completely sealed, but with some openings for heat dissipation.

Referring back to FIG. 2, in some embodiments, power module 230 may further include a battery 238, and a battery insulation wall 239. Battery 238 of power module 230 may be installed in a close vicinity of a surface of main case structure 110. For example, as shown in FIG. 2, battery 238 is installed in a top section of main case structure 110, with one side parallel to the top surface of main case structure 110. Battery 238 may be installed on an installing panel that is attached to an interior surface of main case structure 110. This may facilitate easy removal, assembly, and maintenance of the battery and its neighboring components.

Battery insulation wall 239 helps insulating or separating the battery from transducer module 210, processor module 220, and other components inside main case 200, and eliminating or reducing signal interference caused by the battery on other components. The battery insulation wall may contain one or more materials capable of eliminating or reducing signal interference, such as zinc-coated metal sheets, to further prevent signal interference.

In some embodiments, battery 238 may be installed on battery insulation wall 239, which may be in turn installed on carrier-board baseboard 228. One end of battery insulation wall 239 may be coupled to a top portion of main case structure 110. This configuration facilitates easy maintenance and replacement of the battery when a battery failure or malfunction occurs. It can also eliminate or reduce signal interference caused by the battery on other components.

With reference to FIG. 2, in some embodiments, main case structure 110 may further include one or more handles 240 mounted on its exterior surface, and a sliding means 250 located on its bottom surface, to facilitate easy assembly and disassembly. In some embodiments, sliding means 250 may include one or more sliding bars 252 and sliding wheels 254. In some embodiments, sliding mechanisms 252 and 254 may be sliding bars, sliding slots, ball rollers, or any other sliding means.

Figure 3:
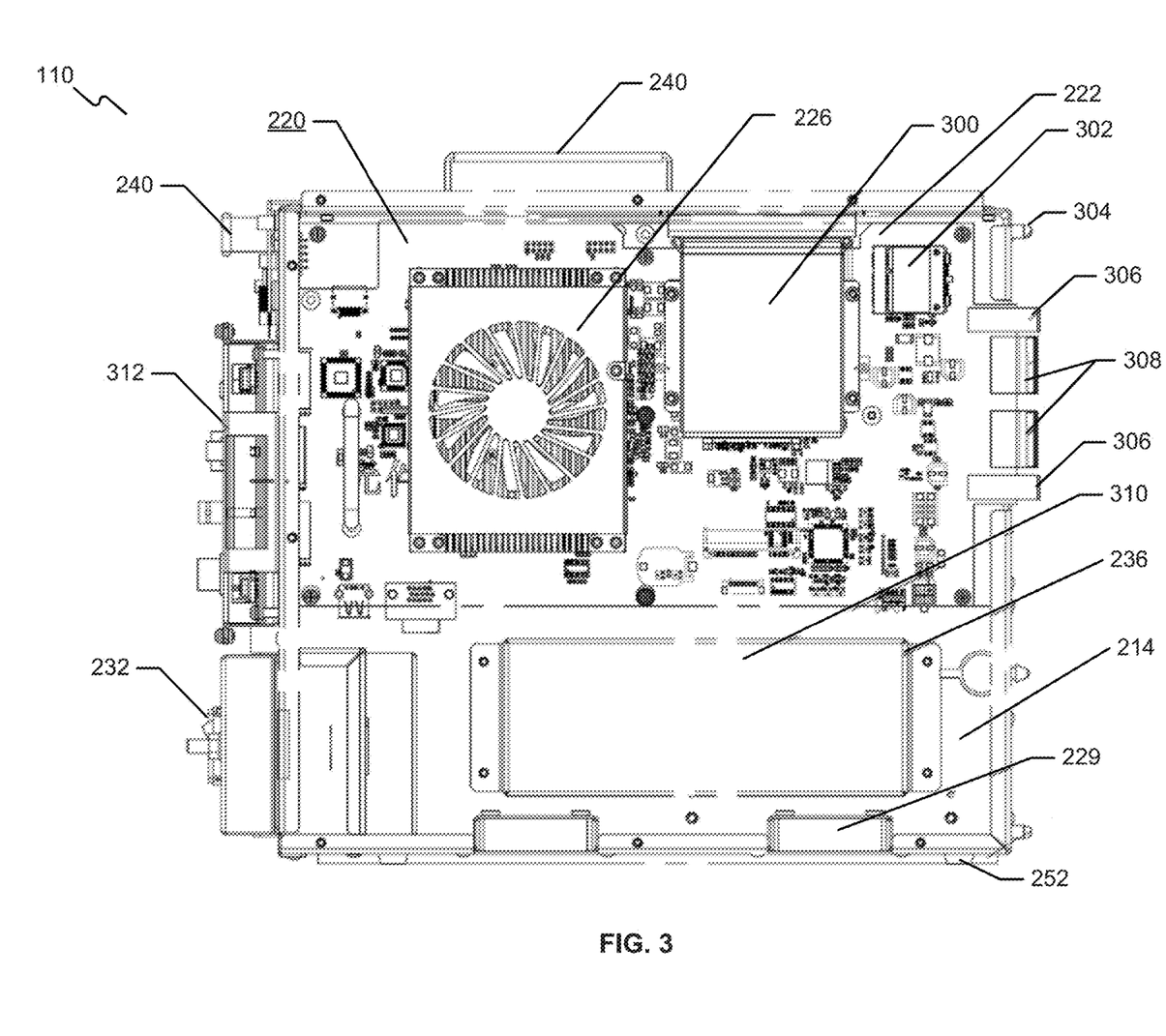
FIG. 3 illustrates a cutaway view of an exemplary main case structure of FIG. 2.

FIG. 3 illustrates a cutaway view of the closed space including processor module 220 in main case structure 110 of FIG. 2. As shown in FIG. 3, the closed space of main case structure 110 includes processor module 220 installed therein. For comparison, the right side of main case structure 110 in FIG. 1 shows components (such as transducer ports coupled to transducer array 150) installed in the other closed space. As shown in FIG. 3, main case structure 110 may further include one or more handles 240, a PC fan 226, a hard drive 300, a Wi-Fi module 302, one or more main-case positioning pillars 304, one or more carrier-board guiding holes 306, one or more carrier-board ports 308, an adapter insulation wall 310, a power supply adapter 236 installed on transducer insulation wall 218, one or more carrier-board fans 229, one or more sliding mechanisms 252, an AC-DC converter 232, and an input/output (I/O) module 312.

With reference to FIG. 3, processor module 220 may include PC module 224 (not shown in FIG. 3), PC fan 226 installed on PC module 224, carrier board module 222, hard drive 300 and Wi-Fi module 302 installed on carrier board module 222, and one or more carrier-board fans 229. Wi-Fi module 302 may be configured to transmit and receive, through a Wi-Fi connection, information such as apparatus control parameters, patient information, video and audio signals. In some embodiments, Wi-Fi module 302 or its components (e.g., a Wi-Fi antenna) may be attached to an exterior surface of main case structure 110.

In some embodiments, main-case positioning pillars 304 are to be coupled to or received by corresponding positioning holes on outer casing 120 (not shown in FIG. 3). Carrier-board guiding holes 306 are to couple with or receive corresponding guiding plugs on outer casing 120 (not shown in FIG. 3). In addition, main case structure 110 may include one or more carrier-board ports 308 to couple with corresponding motherboard ports on outer casing 120 (not shown in FIG. 3). More details will be provided below.

In some embodiments, power supply adapter 236 is installed on transducer insulation wall 218, and is further covered by an adapter insulation wall 310. Transducer insulation wall 218 and adapter insulation wall 310 form a relatively closed space, insulating power supply adapter 236 from causing signal interference on other components installed in main case structure 110.

In some embodiments, one or more carrier-board fans 229 are installed below power supply adapter 236 to dissipate heat generated by components of processor module 220 and adapter 236. To further heat dissipation, one or more ventilation openings may be configured near a bottom and/or top portion of main case structure 110. The size and design of the ventilation openings may vary, depending on working environment conditions and an overall design of the apparatus.

In some embodiments, as shown in FIG. 3, main case structure 110 may include one or more sliding mechanisms 252 (such as sliding bars, sliding slots, sliding wheels, or ball rollers) installed on an exterior bottom surface of main case structure 110. Sliding mechanisms 252 couples with corresponding sliding means (such as sliding slots, sliding bars, sliding wheels, or ball rollers) installed on an interior bottom surface of the outer casing, such that main case structure 110 can slide along the sliding means on the outer casing and move relative to the outer casing. In some embodiments, sliding mechanisms 252 may be installed on an exterior side or top surface of the main case structure 110, and the sliding means on the outer casing may be installed on an interior side or top surface of the outer casing. Any type of sliding mechanisms, such as sliding slots, sliding bars, sliding wheels, or ball rollers, may be used to achieve relative displacement between the main case structure and the outer casing.

In some embodiments, main case structure 110 may include one or more handles 240, with which a user may manually move or pull main case structure 110 into or out of the outer casing. Acting in concert with sliding means 252 on main case structure 110 and the sliding means on the outer casing, handles 240 can facilitate the placement or displacement of main case structure 110 easily. As an alternative to handles 240, in some embodiments, one or more screw-rod mechanisms may be installed between main case structure 110 and outer casing 120, to facilitate the assembly or disassembly of main case structure 110 with or out of outer casing 120. For example, one or more screw-rods are installed on outer casing 120, and main case structure 110 is coupled to one or more screw nuts on the screw-rods. When the screw-rods is rotated, the screw nuts move along the screw-rods linearly, thereby moving main case structure 110 into or out of outer casing 120 along the screw-rods. The screw-rod mechanisms can also help align components on main case structure 110 with those on outer casing 120.

As explained previously, a power-supply filter panel may be installed on AC-DC converter 232. The filter panel and converter 232 form a functioning module, which is placed in a relatively closed insulation box, which can eliminate or minimize signal interference on other components installed in the main case structure 110. In addition, the insulation box is not completely sealed, but with some openings for heat dissipation.

I/O module 312 connects transducer module 210 to processor module 220, facilitates transmission of information and signals between transducer module 210 and processor module 220. In some embodiments, I/O module 312 may include various ports, such as one or more ports for HDMI, USB, VGA, or LAN connection, for transmission of data.

Figure 4:
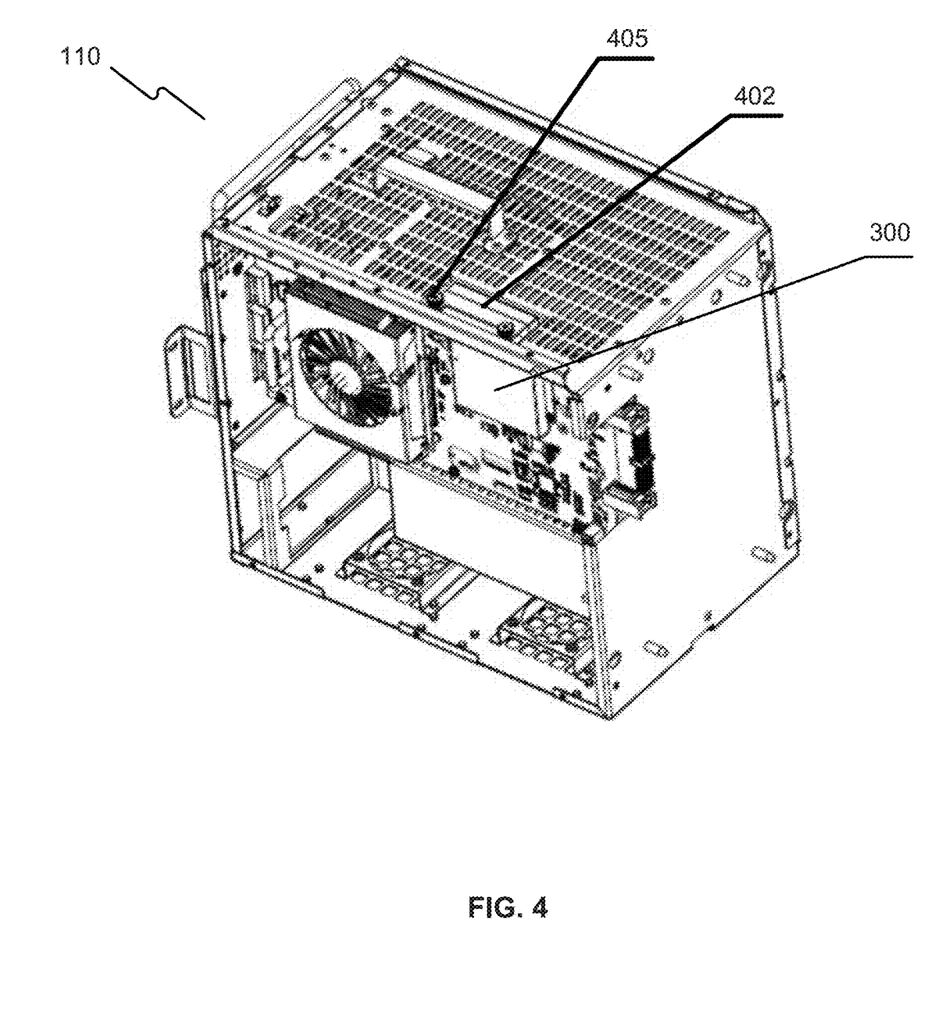
FIG. 4 illustrates another exemplary embodiment of a main case structure of the exemplary ultrasound diagnostic apparatus of FIG. 1.

FIG. 4 illustrates another exemplary embodiment of main case structure 110 of the exemplary ultrasound diagnostic apparatus of FIG. 1. As shown in FIG. 4, main case structure 110 includes a hard drive port 402 on its top portion for receiving hard drive 300, and one or more hard drive screws 404 for securing hard drive 300 onto the top portion of main case structure 110. Comparing to the embodiment shown in FIG. 3 in which hard drive 300 is installed on carrier board module 222, hard drive 300 in the embodiment shown in FIG. 4 is secured onto a place close to an upper surface of main case structure 110. In some embodiments, hard drive 300 may be installed in another place close to a surface of the main case. This arrangement allows easy maintenance and removal of hard drive 300. When a technician maintains or replaces hard drive 300, the technician only needs to pull main case structure 110 out of outer casing 120, unscrew hard drive screws 404, and take hard drive 300 out from hard drive port 402. Further, in some embodiments, hard drive port 402 may be coupled to carrier board module 222 (not shown in FIG. 4), and hard drive 300 may be covered by a hard drive insulation wall to separate the hard drive from other components inside the main case structure, thus further preventing causing signal interference. The insulation wall may be made of materials or coated with materials capable of reducing or substantially eliminating signal interference, such as a zinc-coated metal sheet.

Figure 5:
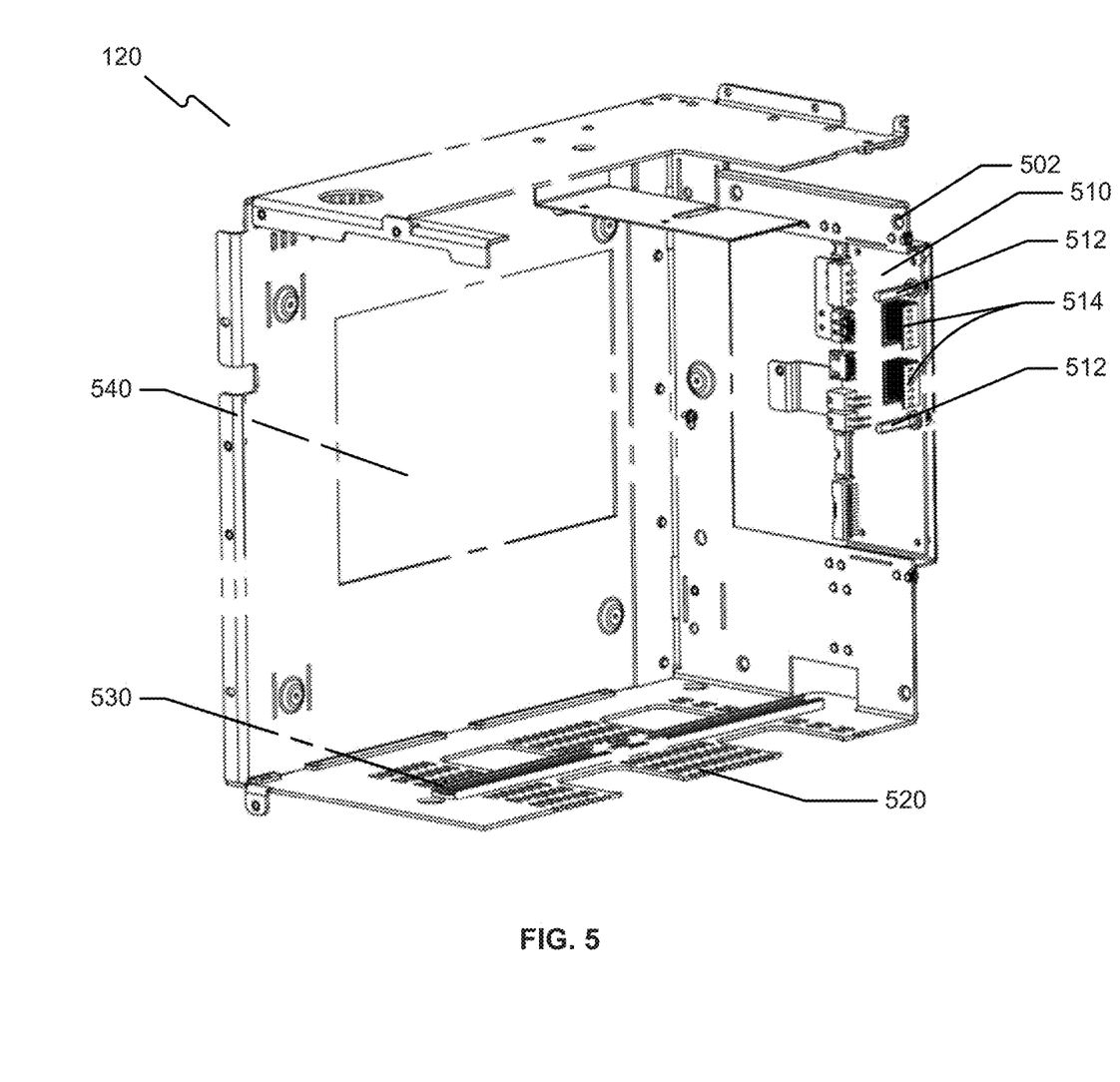
FIG. 5 illustrates a cutaway view of an exemplary outer casing of the exemplary ultrasound diagnostic apparatus of FIG. 1.

FIG. 5 illustrates an exemplary embodiment of outer casing 120 of the exemplary ultrasound diagnostic apparatus of FIG. 1. As shown in FIG. 5, outer casing 120 may include one or more outer-casing positioning holes 502 to be coupled to or receive main-case positioning pillars 304 (as shown in FIG. 3), a motherboard module 510, one or more outer-casing ventilation openings 520, one or more sliding means 530 such as a sliding slot, and one or more transducer windows 540 corresponding to the transducer windows on the main case structure 110 (not shown in FIG. 5).

Motherboard module 510 may be manufactured as part of, or permanently secured onto or detachable from outer casing 120. In some embodiments, as shown in FIG. 5, motherboard module 510 is located on one side of outer casing 120. Motherboard module 510 may further include one or more ports for connecting with output device 130 and input device 140. In some embodiments, motherboard module 510 may include one or more motherboard guiding plugs 512 and one or more motherboard ports 514. During the process of placing/connecting main case structure 110 into/to outer casing 120, motherboard guiding plugs 512 contact and connect with carrier-board guiding holes 306 on main case structure 110 (as shown in FIG. 3) first, accurately aligning and connecting carrier-board ports 308 on main case structure 110 (as shown in FIG. 3) with motherboard ports 514. When a close connection between carrier-board ports 308 and motherboard ports 514 is almost completed, outer-casing positioning holes 502 touch and connect with main-case positioning pillars 304 (as shown in FIG. 3). As carrier-board ports 308 are closely connected with motherboard ports 514, main-case positioning pillars 304 are also closely fitted into outer-casing positioning holes 502, effectively affixing main case structure 110 and outer casing 120 together. Outer casing 120 can exchange information with output device 130 and input device 140 (as shown in FIG. 1) via motherboard module 510. Also, outer casing 120 can provide heat dissipation through its ventilation openings 520 and transducer window 540. Moreover, outer casing 120 can provide main case structure 110 with protection against dust.

With reference to FIG. 5, outer-casing ventilation openings 520 facilitate heat dissipation, and may be arranged near a bottom and/or top portion of outer casing 120. In some embodiments, outer-casing ventilation openings 520 may be configured at a location corresponding to that of ventilation openings on main case structure 110 (not shown in FIG. 5). The size and design of ventilation openings 520 may vary, depending on working environment conditions and an overall design of the apparatus.

Figure 10:
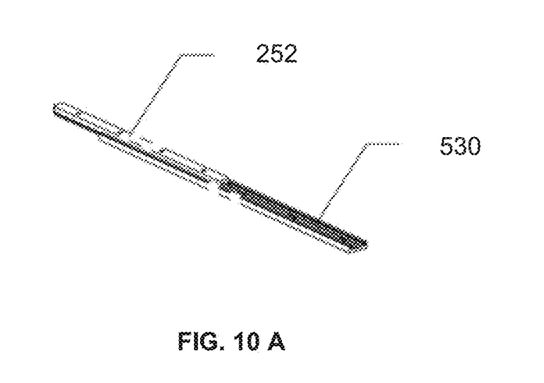
FIGS. 10A, 10B, and 10C illustrate exemplary sliding mechanisms between the exemplary main case structure of FIG. 2 and the exemplary outer casing of FIG. 5.

Sliding means 530 work with sliding mechanisms 252 on main case structure 110 (shown in FIGS. 2 and 3) to facilitate a movement of main case structure 110 relative to outer casing 120 along a track, enabling an easy and accurate assembly of main case structure 110 with outer casing 120 and an easy disassembly of the two. For example, as illustrated in FIG. 10A, sliding mechanism 252 such as a sliding bar on main case structure 110 is coupled to and slides in sliding means 530 such as a sliding slot on outer casing 120, such that structure 110 and casing 120 can slide relative to each other to facilitate placement/displacement of structure 110 into/out casing 120. A sliding mechanism may be installed on a bottom, top, or side exterior surface of main case structure 110 and a corresponding sliding mechanism may be installed on a bottom, top, or side interior surface of outer casing 120, to facilitate relative movement between main case structure 110 and outer casing 120. In some embodiments, main case structure 110 and outer casing 120 may be assembled together by one or more fastening means, such as screws and hinges, and can be disconnected by unfastening the fastening means.

Referring to FIG. 5, when sliding mechanism 252 on main case structure 110 (not shown in FIG. 5) moves along sliding means 530 such as a sliding slot on outer casing 120, the main case structure moves relative to the outer casing for assembly or disassembly. The main case structure may be further pulled out of the outer casing when needed, for example, for purposes of maintenance or repair. Beside facilitating smooth movement of main case structure 110 within outer casing 120, sliding mechanism 252 and sliding means 530 can also help align carrier-board ports 308 on main case structure 110 (as shown in FIG. 3) with motherboard ports 514 on outer casing 120 on a same axis, facilitating an easy and accurate connection between them.

Figure 10B:
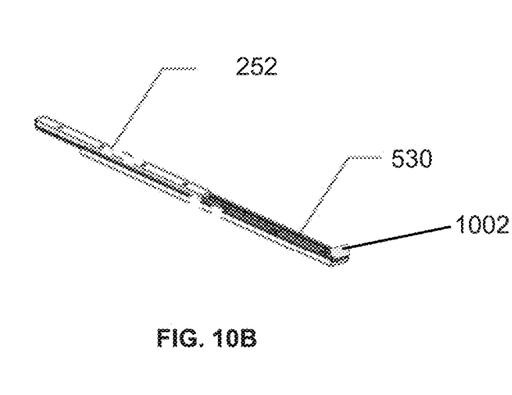

In some embodiments, sliding means 530 may include one or more sliding stoppers 1002 at one of its end sections (as illustrated in FIG. 10B). Sliding stoppers 1002 can be elastic stopping devices (such as elastic flaps) or rigid stopping devices (such as rigid baffles). Sliding stoppers can restrict the sliding movement of main case structure 110 within a certain limit. For example, a sliding stopper may be installed at sliding means 530's end closer to motherboard module 510 (as shown in FIG. 5). The sliding stopper can control a distance of main case structure 110 traveling into outer casing 120, such that the movement of main case structure 110 may be hindered once it reaches the motherboard module. This arrangement can prevent carrier-board ports 308 on main case structure 110 (as shown in FIG. 3) from clashing with motherboard ports 514 on outer casing 120, avoiding damages to ports 208 and 514.

Figure 10C:
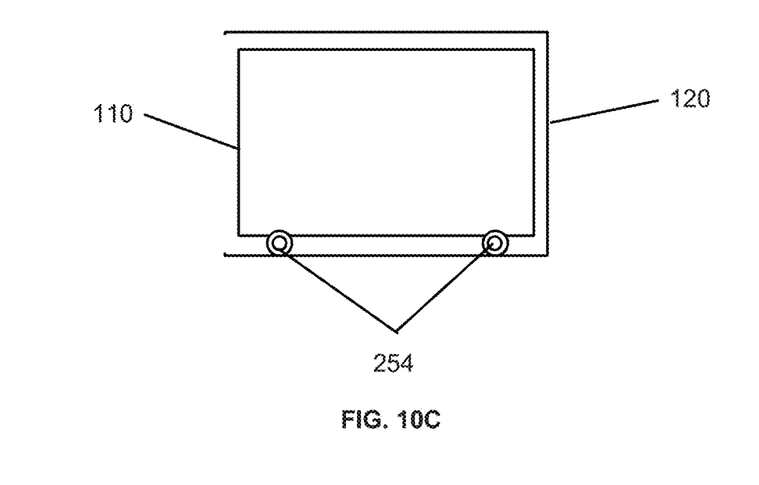

Sliding means 250 on main case structure 110 (shown in FIG. 2) and sliding means 530 on outer case 120 (shown in FIG. 5) can be any type of sliding mechanisms such as one or more sliding bars, sliding slots, sliding tracks, sliding wheels, or ball rollers, etc. For example, as illustrated in FIG. 10C, main case structure 110 includes one or more sliding wheels 254 to move relative to outer casing 120. In some embodiments, sliding wheels 254 facilitate sliding bar 252 to slide in sliding slot 530 smoothly. Sliding wheels 254 may be cylindrical, spherical, and any other shapes. Sliding wheels 254 may be installed on a top, bottom, or side exterior surface of the main case structure, to move along corresponding sliding tracks or slots on the outer casing. In some embodiments, sliding wheels 254 may move on an interior surface of outer casing 120. In some embodiments, a combination of different sliding means, for example, a combination of sliding bars, sliding slots, and sliding wheels, may be used, as illustrated in FIG. 2.

Figure 6:
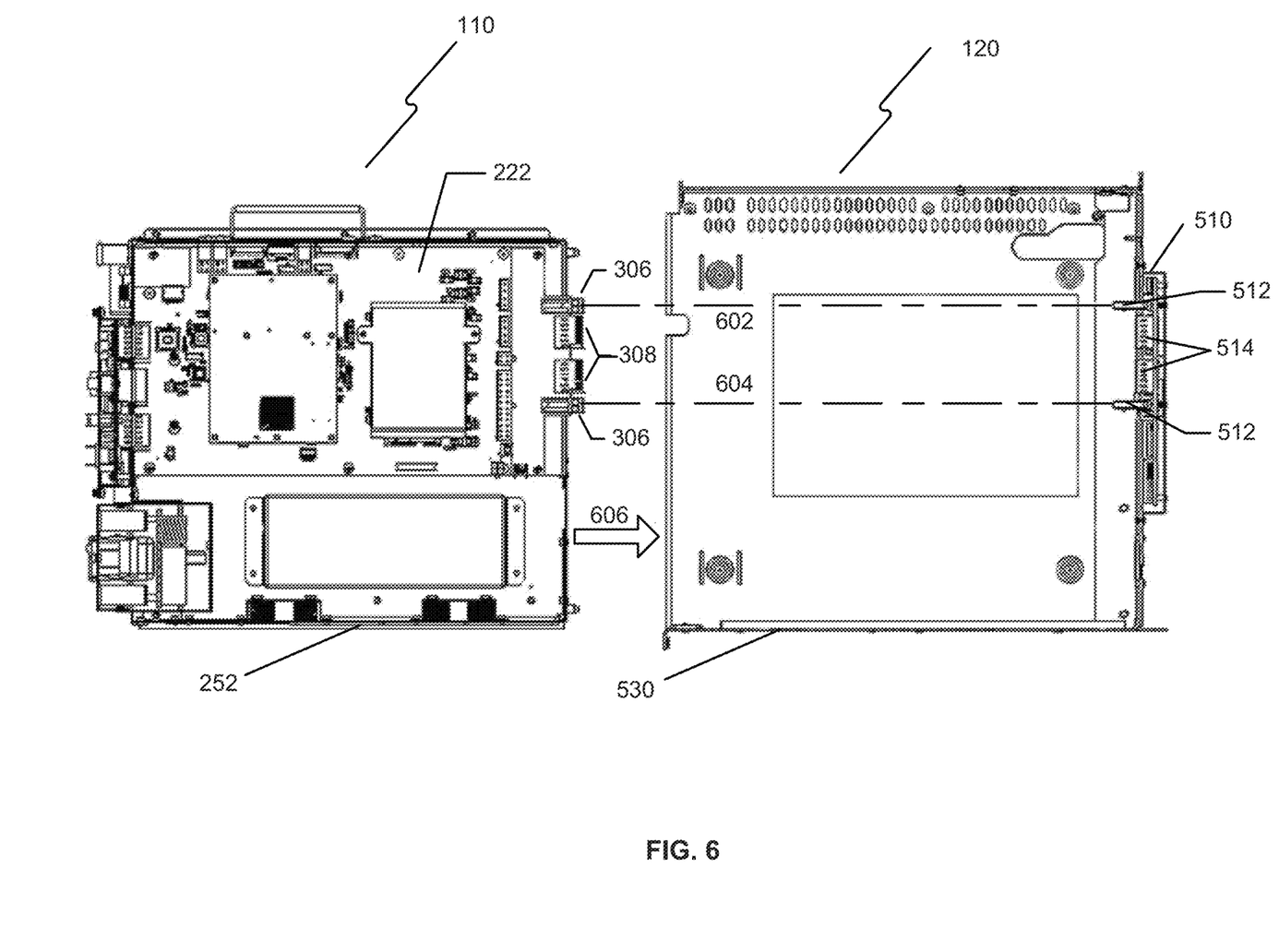
FIG. 6 illustrates an exemplary assembly of the exemplary main case structure of HG. 2 with the exemplary outer casing of FIG. 5.

FIG. 6 illustrates an exemplary assembly of exemplary main case structure 110 of FIG. 2 with exemplary outer casing 120 of FIG. 5. As shown in FIG. 6, main case structure 110 includes carrier board module 222, one or more carrier-board guiding holes 306, one or more carrier-board ports 308, and one or more sliding bars 252 on its bottom exterior surface. Outer casing 120 includes motherboard module 510, and one or more sliding slots 530 on its bottom interior surface. Motherboard module 510 further includes one or more motherboard guiding plugs 512 and one or more motherboard ports 514. During assembly, main case structure 110 slides along a sliding track into (606) outer casing 120 via sliding bars 252 fitting into and sliding along sliding slots 530, carrier-board guiding holes 306 connecting with and receiving (602 and 604) motherboard guiding plugs 512, carrier-board ports 308 being accurately aligned with and interconnected with motherboard ports 514, and thus ensuring that carrier board module 222 accurately interconnects with motherboard module 510.

In some embodiments, motherboard module 510 and carrier board module 222 may be connected by other fastening means, for example, screws and fastening clamp, to secure the attachment. Outer casing 120 houses main case structure 110, preventing dust in the environment from landing on main case structure 110 and its components. In some embodiments, one or both of outer casing 120 and the casing of main case structure 110 may contain one or more materials capable of reducing or eliminating signal interference.

Figure 7:
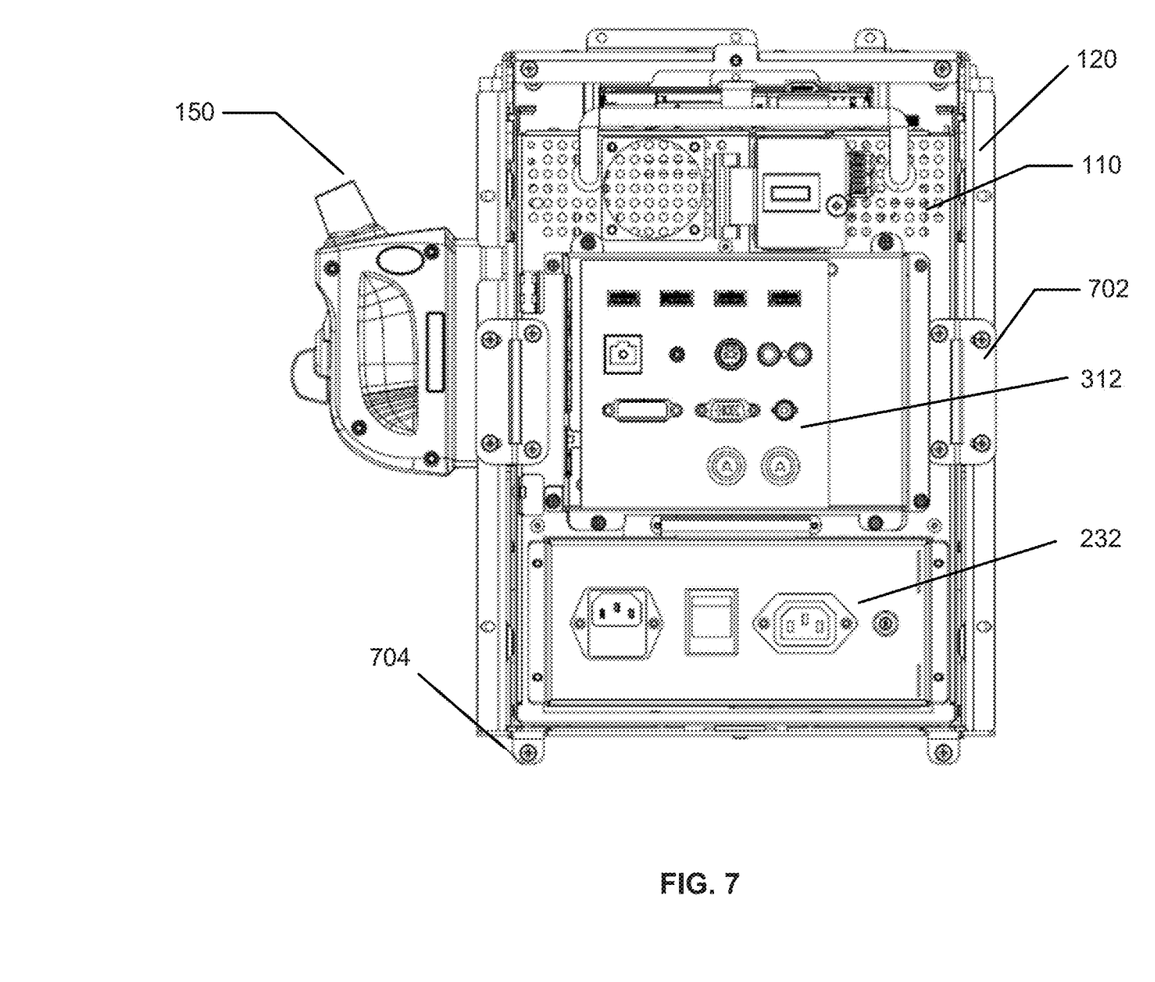
FIG. 7 illustrates a rear view of an exemplary assembly of FIG. 6.

FIG. 7 illustrates a rear view of an exemplary assembly of FIG. 6. As shown in FIG. 7, after main case structure 110 is assembled with outer casing 120 to form an assembly, one or more fastening means 702 may be used to securely fasten main case structure 110 and outer casing 120 together. Various fastening means may be utilized, for example, screws and fastening clamps.

An I/O module 312 is installed onto a rear side of main case structure 110. As previously discussed, I/O module 312 facilitates transmission of information and signals between the transducer module (connected to transducer array 150) and the processor module. In some embodiments, I/O module 312 may include various ports, such as one or more ports for HDMI, USB, VGA, or LAN connection, for data transmission. Below I/O module 312, an AC-DC converter 232 and power-supply filter panel 234 (not shown in FIG. 7) are installed on main case structure 110. One or more fastening means 704 are installed beneath outer casing 120 for fastening the assembly to a moving platform, which may have one or more apparatus wheels 160 (as shown in FIG. 1).

Figure 8:
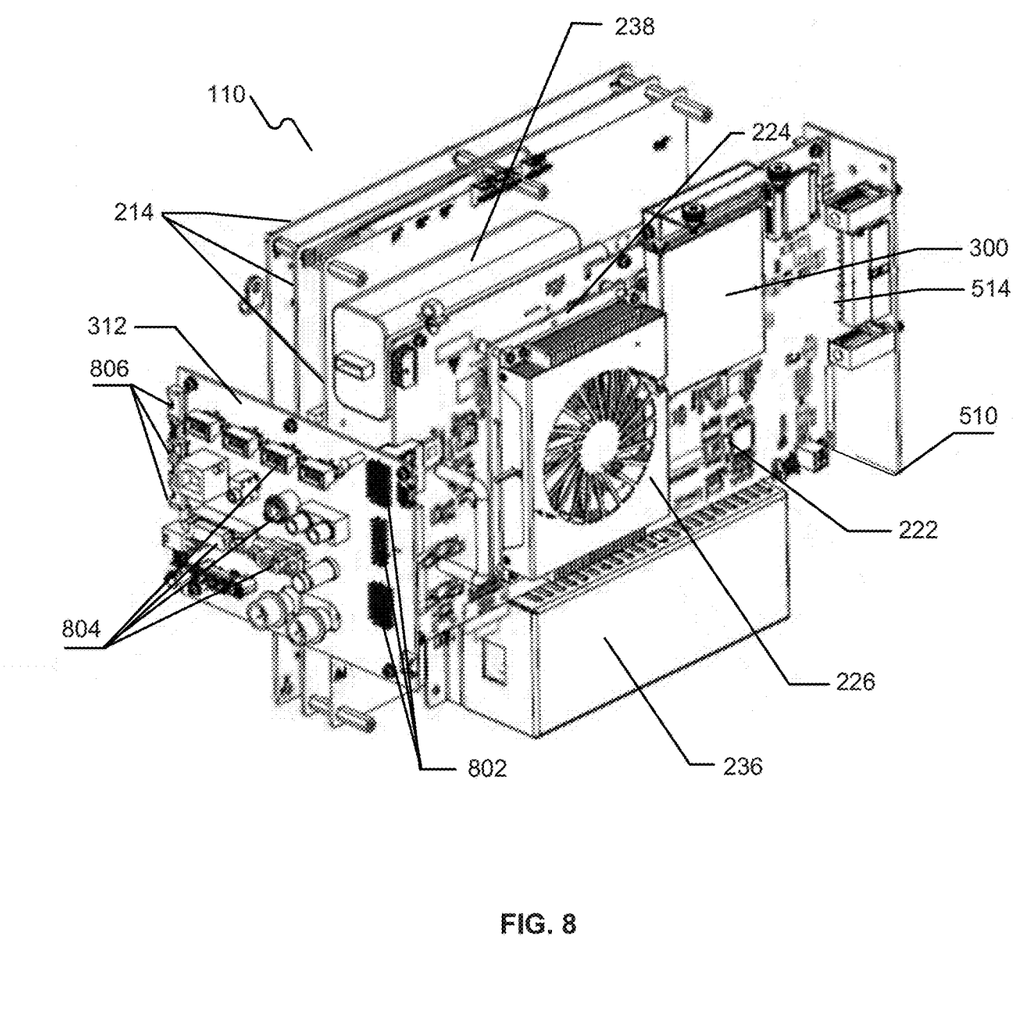
FIG. 8 illustrates a side view of an exemplary structural connections among components of the exemplary main case structure of FIG. 2 and those of the exemplary outer casing of FIG. 5.

FIG. 8 illustrates a side view of an exemplary structural connections among components of main case structure 110 of FIG. 2 and those of outer casing 120 of FIG. 5. As shown in FIG. 8, main case structure 110 includes one or more transducer panels 214, a battery 238, a PC module 224, a PC fan 226 installed on PC module 224, a hard drive 300, a carrier board module 222, a power-supply adapter 236, and an I/O module 312. I/O module 312 may further include one or more board-to-board connectors 802, one or more user interface ports 804, and one or more information ports 806. Components on main case structure 110 interconnect and communicate data with components on outer casing 120 via motherboard ports 514 on motherboard module 510. In some embodiments, information ports 806 may include one or more ultrasound signal ports, control-parameter signal ports, analog signal ports, digital signal ports, and power-supply signal ports, or any combination thereof, to transmit data and information.

To facilitate an easy separation or disassembly of main case structure 110 from outer casing 120, the separation or disassembly process does not need to unplug or plug wires connecting components of structure 110 with components of outer casing 120. As illustrated in FIG. 8, I/O module 312 connects transducer panels 214 to carrier board module 222. Transducer panels 214 connect with information ports 806 on I/O module 312 via various data wires or cables. And carrier board module 222 inter-plugs in and connects with I/O module 312 via board-to-board connectors 802. When a user needs to read ultrasound diagnostic data, the user can do so by connecting an exterior read device to user interface ports 804 (such as ports for VGA, HDMI, USB, LAN, etc.) on I/O module 312. In some embodiments, I/O module 312 transmits data and signals among board-to-board connectors 802, user interface ports 804, and information ports 806, via data wires and cables connecting those ports.

Moreover, carrier board module 222 performs data transmission with motherboard ports 514 via inter-plug-in communications. In some embodiments, as illustrated in FIG. 8, I/O module 312 and motherboard module 510 are arranged and installed on the main case structure's two opposite sides perpendicular to transducer panels 214 and carrier board module 222. This arrangement allows data transmission through I/O module 312 and motherboard module 510 installed on two ends of the main case structure, further reducing signal interference. This arrangement can also facilitate easy and quick disassembly or separation of main case structure 110 from outer casing 120, by unplugging or detaching I/O module 312 and motherboard module 510 from their counterparts, without unplugging various wires and cables and without obstacles caused by various wires and cables.

By coupling carrier board module 222 to I/O module 312 installed on main case structure 110 and motherboard module 510 installed on outer casing 120, PC module 224 installed on carrier board module 222 can obtain from and transmit data to devices connected to I/O module 312 and motherboard module 510, such as output device 130, input device 140, and transducer array 150. For example, information ports 806 transmit information, such as ultrasound digital information, control-parameter information, electrical pulse information, etc. to carrier board module 222. Carrier board module 222 in turn transmits the information to PC module 224. In addition, motherboard module 510 transmits information (such as video or image information, parameter information, audio information, etc.), received via motherboard ports 514, to output device 130 for display or output. Furthermore, motherboard ports 514 transmit information (such as control-parameter information, input information, etc.), received from input device 140 and output device 130, to carrier board module 222, which transmits the received information to PC module 224.

During an operation of ultrasound diagnostic apparatus 100, a user controls a transducer in transducer array 150 to emit/receive ultrasound electrical signals to/from a patient's body, via transceivers on transducer panels 214. The transceivers transmit the ultrasound electrical signals to an information-processing module on transducer panels 214 for converting the ultrasound electrical signals into digital information. The information-processing module transmits the digital information to carrier board module 222, via information ports 806 on I/O module 312. Carrier board module 222 passes the received digital information to data-processing units (such as CPU, GPU, memory, etc.) on PC module 224 for data processing. PC module 224 transmits the processed digital information to hard drive 300 for storage, and transmit the processed information (such as video/image information, parameter information, etc.) to output device 130 (such as a display) via motherboard ports 514 and motherboard module 510. The user obtains from output device 130 various needed information, such as image data information, video, detection parameters of the patient's various organs, environment parameters, apparatus parameters, etc. The user can control apparatus 100, input information on apparatus 100, or inquire information from apparatus 100 based on the user's experience and the information presented on output device 130. The user can achieve the above tasks by inputting various control parameters for apparatus 100 on input device 140. Input device 140 transmits the inputted control parameters to PC module 224 installed in main case structure 110, via various data cables, motherboard ports 514, and motherboard module 510. PC module 224 controls and reconfigures various modules and their components based on the received control parameters and/or pre-configured parameters. For example, PC module 224 can control and adjust one or more transmission parameters such as transmission frequencies, transmission time, and/or transmission angles of transducers in array 150, via the transceivers on transducer panels 214. PC module 224 can also perform data input and output via motherboard module 510 and motherboard ports 514.

In the preceding specification, the invention has been described with reference to specific exemplary embodiments. It will, however, be evident that various modifications and changes may be made without departing from the broader spirit and scope of the invention as set forth in the claims that follow. The specification and drawings are accordingly to be regarded as illustrative rather than restrictive. Other embodiments of the invention may be apparent to those skilled in the art from consideration of the specification and practice of the invention disclosed herein.

What is claimed is:

1. An ultrasound diagnostic apparatus having a plurality of components, comprising:
   an outer casing including:
      a motherboard module having one or more motherboard guiding plugs and one or more motherboard ports installed thereon to facilitate the assembly, and
      a first outer-casing sliding device; and
   a main case structure being housed by the outer casing, wherein the main case structure comprises a main casing to form an internal space for hosting:
      an I/O module attached to a first side of the main casing,
      a power-supply module to receive a power supply and provide the power supply to at least one of the plurality of components,
      a transducer panel module coupled to the I/O module and having a transceiver and a transducer information-processing module installed thereon, the transceiver being coupled to a transducer to emit and receive ultrasound electrical signals and the transducer information-processing module converting the received ultrasound electrical signals into digital information,
      a carrier board module coupled to the I/O module and to the transducer information-processing module via the I/O module and having a PC module installed thereon to process the converted digital information and transmit the processed digital information to an output device coupled to the one or more motherboard ports, the PC module being coupled to the motherboard module,
      one or more carrier-board guiding holes to receive the one or more motherboard guiding plugs and guide the assembly,
      one or more carrier-board ports to inter-plug in the one or more motherboard ports and facilitate data communications between the motherboard module and the carrier board module, and
      a first main-case sliding device located on a second side of the main casing and coupled with the first outer-casing sliding device of the outer casing to slide in the first outer-casing sliding device, causing the main case structure to move relative to the outer casing along the first outer-casing sliding device during the assembly and disassembly;
   wherein the motherboard module and the I/O module are installed on the main case structure's two opposite sides perpendicular to the transducer panel module and the carrier board module to allow the easy assembly and disassembly.

2. The ultrasound diagnostic apparatus according to claim 1, further comprising:
   an input device coupled to the one or more motherboard ports to receive control parameters provided by a user, wherein the PC module is coupled to the input device via the motherboard module and the one or more motherboard ports to receive the inputted control parameters.

3. The ultrasound diagnostic apparatus according to claim 2, wherein:
   the PC module controls the transducer by:
      adjusting one or more transmission parameters relating to a transmission frequency, a transmission time, and/or a transmission angle based on the received control parameters, and
      transmitting the adjusted one or more transmission parameters to the transceiver via the I/O module.

4. The ultrasound diagnostic apparatus according to claim 1, wherein:
   during the assembly, the main case structure slides into the outer casing along the first outer-casing sliding device to enable the one or more motherboard guiding plugs to plug into the one or more carrier-board guiding holes and enable the one or more carrier-board ports to align with the one more motherboard ports for the inter-plugging in.

5. The ultrasound diagnostic apparatus according to claim 4, wherein:
   the outer casing further includes one or more outer-casing positioning holes; and
   the main case structure further includes one or more main-case positioning pillars to fit into the one or more outer-casing positioning holes when the one or more carrier-board ports inter-plug into the one more motherboard ports, affixing the main case structure with the outer casing together.

6. The ultrasound diagnostic apparatus according to claim 1, wherein:
   the first outer-casing sliding device includes a sliding stopper to stop the first main-case sliding device and restrict the main case structure to move inside the outer casing within a certain range.

7. The ultrasound diagnostic apparatus according to claim 1, wherein:
   the sliding stopper is located near the first outer-casing sliding device's end close to the outer casing's side installing the motherboard module having the one more motherboard ports to allow the inter-plugging in between the
   one or more carrier-board ports and the one more motherboard ports on the main case structure and prevent the one or more carrier-board ports from clashing with the one more motherboard ports.

8. The ultrasound diagnostic apparatus according to claim 1, wherein:
   the main case structure further includes a second main-case sliding device to slide on an interior surface of the outer casing and facilitate the first main-case sliding device to slide in the first outer-casing sliding device smoothly.

9. The ultrasound diagnostic apparatus according to claim 8, wherein:
   the outer casing further includes a second outer-casing sliding device to allow the second main-case sliding device to slide therein.

10. The ultrasound diagnostic apparatus according to claim 1, wherein:
    the outer casing further includes one or more screw-rods installed between the outer casing and the main case structure, the main case structure being coupled to one or more screw nuts on the screw-rods, and when the screw-rods is rotated, the one or more screw nuts move along the screw-rods linearly to move the main case structure into or out of the outer casing along the screw-rods.

11. The ultrasound diagnostic apparatus according to claim 1, wherein:
the main case structure further includes a transducer insulation wall between the transducer panel module and the carrier board module to separate the internal space of the main case structure into two relatively closed spaces, at least one end of the transducer insulation wall being mounted onto an interior surface of the main case structure;
the first relatively closed space includes the transducer panel module, the transceiver coupled to the transducer, and the transducer information-processing module; and
the second relatively closed space includes the carrier board module, the PC module, the one or more carrier-board ports, and the power-supply module.

12. The ultrasound diagnostic apparatus according to claim 11, wherein:
the transducer insulation wall substantially surrounds the first relatively closed space or the second relatively closed space and includes a material capable of eliminating or reducing signal interference between components installed in the first relatively closed space and components installed in the second relatively closed space.

13. The ultrasound diagnostic apparatus according to claim 1, wherein the I/O module comprises:
one or more board-to-board connectors to couple the carrier board module with the I/O module to enable an inter-plug-in communication between the carrier board module having the PC module and the I/O module;
one or more user interface ports coupled to a user device for reading data from the ultrasound diagnostic apparatus; and
one or more information ports coupled to the transducer panel module to transmit data between the transducer panel module and the carrier board module having the PC module,
wherein the one or more board-to-board connectors, the one or more user interface ports, and the one or more information ports transmit data between them via one or more data cables on the I/O module.

14. The ultrasound diagnostic apparatus according to claim 1, wherein:
the power-supply module includes a battery and a battery insulation wall insulating the battery from other components installed in the main case structure;
the battery insulation wall includes a material capable of eliminating or reducing signal interference caused by the battery on other components in the main case structure.

15. The ultrasound diagnostic apparatus according to claim 14, wherein:
the battery is installed in a close vicinity of a surface of the main case structure to facilitate easy removal, assembly, and maintenance of the battery and its neighboring components.

16. The ultrasound diagnostic apparatus according to claim 1, wherein the power-supply module comprises:
a AC-DC converter; and
a power-supply filter panel installed on the AC-DC converter to insulate signal interference caused by the AC-DC converter.

17. The ultrasound diagnostic apparatus according to claim 16, wherein:
the AC-DC converter and the power-supply filter panel are placed inside an insulation box to further eliminate or minimize signal interference on other components installed in the main case structure.

18. The ultrasound diagnostic apparatus according to claim 16, wherein the main case structure further comprises:
a hard drive; and
a hard drive port located near a top surface of the main case structure to receive the hard drive and allow easy removal of the hard drive.

19. The ultrasound diagnostic apparatus according to claim 1, wherein:
the main case structure further includes one or more ventilation openings aligned with one or more fans in the main case structure for heat dissipation.

20. The ultrasound diagnostic apparatus according to claim 1, wherein:
the outer casing further includes a transducer window for the transducer to pass through and couple with a transducer port on the transducer panel module installed on the main case structure.

* * * * *